United States Patent [19]

Ford

[11] 4,257,259
[45] Mar. 24, 1981

[54] CONTINUOUS ANALYSIS OF BEVERAGES

[75] Inventor: Gregory A. Ford, Bartlesville, Okla.

[73] Assignee: Phillips Petroleum Company, Bartlesville, Okla.

[21] Appl. No.: 96,109

[22] Filed: Nov. 20, 1979

Related U.S. Application Data

[62] Division of Ser. No. 883,015, Mar. 3, 1978, Pat. No. 4,204,962.

[51] Int. Cl.³ ............................................. G01N 31/08
[52] U.S. Cl. .................................................. 73/61.1 C
[58] Field of Search .......................... 73/61.1 C, 23.1; 210/34 C, 198 C

[56] References Cited

U.S. PATENT DOCUMENTS 4,067,226 1/1978 Ririe ...................................... 73/23.1

Primary Examiner—Gerald Goldberg
Assistant Examiner—Joseph W. Roskos

[57] ABSTRACT

A method and analysis system for the continuous on-stream chromatographic analysis of beverages such as beer. Also disclosed are novel bypass filter devices that are especially suitable for use in the analysis system.

9 Claims, 11 Drawing Figures

CONTINUOUS ANALYSIS OF BEVERAGES

This application is a division of application Ser. No. 883,015 filed Mar. 3, 1978, now U.S. Pat. No. 4,204,962.

The present invention relates to the analysis of beverages. In one aspect this invention relates to a system for determining the content of constituents such as carbon dioxide, ethyl alcohol, and carbohydrates in alcoholic beverages such as beer.

In the production of alcoholic beverages, such as beer, it is often necessary to monitor the alcohol, carbon dioxide, or carbohydrate content of beer products. Conventionally, this has been done by conducting analysis on samples of various finished batches of product beer. Such a process is very time consuming and does not provide a very effective means of process control. There thus is a need in the alcoholic beverage industry for a continuous on-stream analysis system such as the liquid chromatographic analysis systems used in other chemical processes.

However, the higher molecular weight materials such as the higher molecular weight carbohydrates in beer, have been found to interfere with the continuous chromatographic separation of samples when using conventional liquid chromatography columns. Also degassing, the evolution of carbon dioxide bubbles, has heretofore interfered with the practical use of liquid chromatographic separation in the continuous analysis of alcoholic beverages such as beer.

It is thus an object of the present invention is to provide a method for the continuous on-stream liquid chromatographic analysis of beverage process streams.

Another object of the present invention is to provide an analytical system for the continuous on-stream liquid chromatographic analysis of beverage process streams.

Still another object of the present invention is to provide novel filtration devices that are particularly useful in the present inventive system for the continuous on-stream analysis of beverages.

Other objects, advantages, and features of this invention will be apparent from the following disclosure and the accompanying drawings.

In accordance with the instant invention a plurality of sample streams from one or more process lines are, while under pressure sufficient to prevent significant degassing of the beverage, individually passed through a filter means which separates said beverage into a retentate containing materials of greater than a preselected molecular weight and a filtrate comprising substantially materials of less than said preselected molecular weight, and said filtrate, while under pressure sufficient to prevent significant degassing of the filtrate, is passed to a liquid column chromatographic analysis system wherein a sample of said filtrate is subjected to chromatographic analysis under pressure sufficient to prevent significant degassing of the filtrate sample. (The phrase "significant degassing" as used herein is intended to denote degassing which would interfere with the liquid column chromatographic analysis of the beverage.)

In accordance with one embodiment of this invention there is provided an analytic system for continuous beverage analysis which comprises (1) one or more sample stream lines each adapted to be connected to a separate process line containing beverage to be analyzed, (2) a bypass filter means capable of separating a stream of beverage into a retentate and a filtrate containing no significant amounts of materials having more than a preselected molecular weight, (3) a manifold means in fluid communication with each sample stream line, (4) an outlet line providing fluid communication between said manifold means and said bypass filter means, (5) a pump in each sample stream line at a point sufficiently below the juncture of the process line and the sample stream line to assure that when the pump is operated there will not be any significant degassing of the beverage, (6) a pump in said outlet line for pumping beverage to said bypass valve, (7) a recycle line providing fluid communication between each sample stream line back to the respective process line at a point between said manifold and said pump in said sample stream line, (8) recycle valve means associated with each sample stream line for controlling whether the sample stream will flow to the manifold or the process line, (9) a retentate line providing for flow of retentate from said bypass filter,

(10) an analyzer means capable of measuring the amount of at least one chosen low molecular weight material in the beverage filtrate,

(11) a filtrate line providing for flow of filtrate from the bypass filter to said analyzer means,

(12) a filtrate disposal line providing for flow of unanalyzed filtrate from said analyzer, and

(13) back pressure regulator means connected to said filtrate disposal line and said retentate line so as to assure that the beverage in said system is maintained under sufficient pressure to prevent significant degassing of the beverage.

In another embodiment of the present invention there are provided novel bypass filters that are particularly useful in the analytical system of the present invention.

In still another embodiment of the present invention there is provided an improved self-cleaning filter apparatus that is particularly useful in the analytical system of the present invention.

A further understanding of the present invention will follow from a study of the drawings in which.

Figure 1:
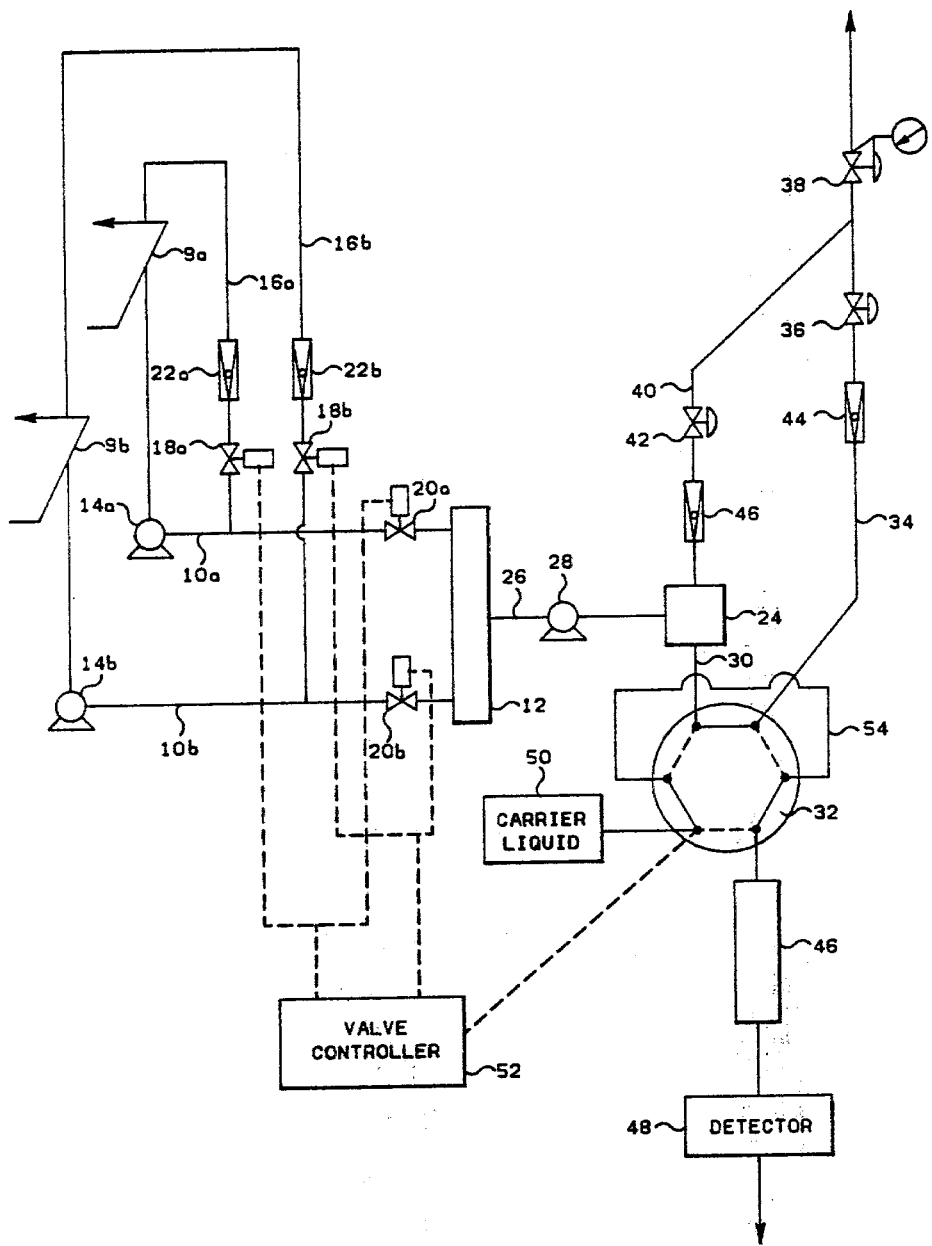
FIG. 1 is a schematic representation of an analytical system of the present invention for the continuous analysis of beverage.
Figure 2:
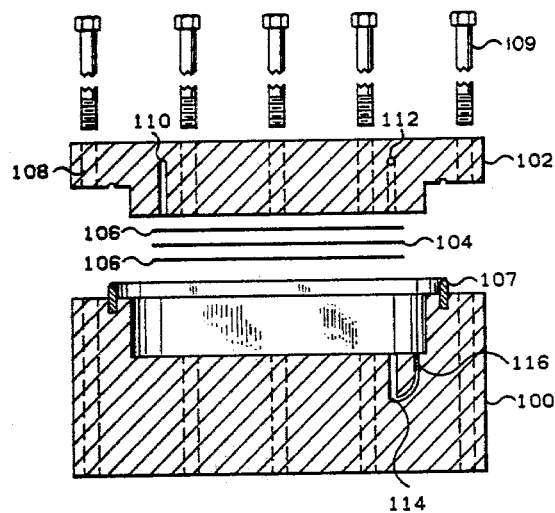
FIG. 2 is a cross-sectional exploded view of a new improved bypass filter which is included as an embodiment of the present invention.

Now referring to FIG. 1 in detail, there is shown a plurality of sample stream conduits 10a and 10b each connected to respective beer process conduits 9a and 9b. Each sample stream conduit is connected in fluid communication with manifold 12.

Sample stream conduits 10a and 10b each contain a respective pump 14a and 14b located sufficiently below the juncture of the respective sample stream conduit with the respective process conduit to assure that no significant degassing of the beer will occur when the pump is in operation.

Attached to sample stream conduits 10a and 10b are respective recycle conduits 16a and 16b. The recycle conduits provide for recycling of beer from the respective sample stream conduit at a point between the respective pump in the sample stream line and the manifold means 12. Each recycle conduit contains a respective valve 18a and 18b. Also each sample stream contains a respective valve 20a and 20b. Valves 18a and 20a serve to control whether sample liquid will be pumped to the manifold 12 or back to the respective process line. For convenience in monitoring the system flow rate, meters 22a and 22b are provided in recycle conduits 16a and 16b.

A bypass filter means 24, which will be described in more detail below, is connected in fluid communication with the manifold 12 by means of manifold outlet conduit 26. A pump 28 is located in conduit 26.

A conduit 30 provides a path for flow of filtrate from the bypass filter 24 to a sample valve 32 of an analyzer system.

The analyzer system comprises the sample valve 32, which can be any suitable sample valve, including for example a slide valve of the type described in U.S. Pat. No. 2,846,121, the disclosure of which is incorporated herein by reference. An especially preferred type of sample valve and the type illustrated schematically as item 32 in FIG. 1 is the six-port, two-position valves of the type disclosed in U.S. Pat. Nos. 3,140,615 and 3,492,873, the disclosures of which are incorporated herein by reference. Air actuated, six-port, two-position valves of this type can be obtained from Applied Automation, Inc. located in Bartlesville, Oklahoma.

Connected to a first exit port of sample valve 32 is a filtrate disposal conduit 34 providing a path for unanalyzed filtrate to flow out of the system. Valve means 36 is located in conduit 34 for controlling the pressure of the liquid between said valve and sample valve 32. Another valve means 38 is located downstream of valve means 36 for maintaining the total system under a chosen pressure.

A conduit means 40 provides fluid communication between the retentate from bypass filter 24 and conduit 34 at a point between valve means 36 and 38. A valve means 42 is located in conduit means 40 for maintaining the back pressure in the bypass filter 24 at a level sufficient to obtain the desired amount of filtrate production. Conduit means 34 and 40 each respectively contain flow rate meters 44 and 46.

A liquid chromatography column 46 suitable for the liquid chromatographic separation of the filtrate components is connected to a second exit port of the sample valve 32. A detector means 48 is connected to the outlet end of the column 46. The detector means can be any suitable means capable of detecting a property of the filtrate constituents that are to be monitored. Typical detectors include refractometers and ultraviolet detectors.

Carrier liquid for forcing a specific volume of the filtrate through the column 46 is provided to the sample valve 32 under pressure from a carrier liquid source 50 in a manner known in the art.

Finally, a valve controller means 52 is provided which controls the operation of valves 18a, 18b, 20a, 20b, and 32. An example of a suitable valve controller means can be found in U.S. Pat. No. 3,069,898, the disclosure of which is incorporated herein by reference.

Preferably all the valves in the system are air actuated. It is also preferred for the conduits transporting the samples between the process line and the analyzer means to be of about 0.25 inch in internal diameter. It is further preferred that all valves in the flow streams have sufficiently large orifices as to not cause pressure drops that would result in significant degassing of the liquid. Also, to guard against undue pressure drop, it is preferred that all fittings and rotameters have an internal diameter of about 0.25 inch.

It is further preferred that all fittings and valves be of the Swagelok ® type so that the system can be easily disassembled for washing and sterilizing.

The operation of the system illustrated in FIG. 1 will now be described. For the purpose of this description, first analysis of the beer in process stream 9b will be described. To accomplish this, valve 18b is closed and valve 20b is opened so that the beer from the process line 9b flows into the manifold 12. Contemporaneously, valve 20a is closed and valve 18a is opened so that beer from process line 9a will not flow into manifold 12, but will be recycled to line 9a via conduit 16a.

With the aforementioned valves thus positioned, beer from process line 9b is pumped through the manifold 12 and conduit 26 into bypass filter 24. Valve 42 is set in a position which provides sufficient back pressure on the retentate outlet of the bypass valve to obtain a selected amount of filtrate flow in conduit 30.

The filtrate flows through conduit 30 into sample valve 32 which is initially positioned such that the filtrate flows via a first passageway in the sample valve to the filtrate disposal conduit 34. In this first position of the sample valve, the carrier liquid flows through the sample loop 54, out of the second outlet of the sample valve 32, and into the column 46. At a selected point in time, the sample valve is switched from its first position to its second position; whereupon, filtrate from line 30 will pass into the sample valve through the sample loop 54 and then out the first outlet of the sample valve. At another selected point in time, the sample valve is then returned to its first position; whereupon, the known volume of filtrate trapped in the sample loop 54 will be forced from the sample valve 32 and through the column 46 by the carrier liquid. As the components of the filtrate elute from the column, they are monitored by detector 48.

After a suitable sample of the filtrate has been trapped by the sample valve, the positions of valves 18a, 18b, 20a, and 20b will be reversed so that beer from process stream 9b will be recycled via conduit 16b and beer from process stream 9a will pass via conduit 10a into the manifold 12 and then through the same flow path previously described for the beer of process stream 9b so that the beer filtrate of process stream 9b will be subjected to identical analysis. The cycle thus described of sampling one process line and then the other can be repeated periodically as described.

The flow of filtrate exiting the sample valve 32 via the first outlet of the sample valve and retentate exiting the bypass filter, in the illustrated system combine and are passed to some suitable point of disposal or point for reuse in the beer process.

The bypass filter employed in the present invention can be any suitable filter capable of producing, under the condition of the inventive system, a filtrate comprising substantially materials having molecular weights sufficiently low so as not to seriously affect the ability of the chromatography column to be used for repeated separations. Generally, it is suitable if the filtrate comprises substantially materials of less than 10,000 molecular weight.

One bypass filter that can be employed in the inventive system illustrated in FIG. 1 is the high volume ultrafiltration system sold commercially as the Pellicon Cassette System (Pellicon is a registered trademark of Millipore Corporation of Bedford, Mass.). That bypass filter comprises a top member, a bottom member, a sample inlet means, a retentate outlet means, a filtrate outlet means, at least one ultrafiltration packet positioned between said top member and said bottom member, a mesh spacer above and below each said packet means for clamping said at least one packet and the corresponding mesh spacers between said top and bottom members, means to flow liquid sample through each mesh spacer along the adjoining surface of the adjoining packet and then out said retentate outlet means, and means to allow filtrate from within each said packet to flow out of said bypass filter via said filtrate outlet means.

A preferred bypass filter which is a further embodiment of this invention is an improvement upon the above mentioned type of high volume ultrafiltration system. The improvement comprises (1) a sealing means which when clamped between said top and bottom means will provide a fluid tight area surrounding said at least one ultrafiltration packet and the corresponding mesh spacers and (2) means for removing from the bypass filter liquid which accumulates within that fluid tight area. This improvement will assure that one can maintain control over any liquid which passes out of the stack of at least one ultrafiltration packet and corresponding spacers to assure that there is no leakage of liquid from the body of the filter. Preferably, the means for removing liquid which accumulates within the fluid tight area comprises means for directing that liquid to the retentate outlet means. Such an improvement thus insures that the system will be more sanitary since the presence of leakages of beverage will be minimized.

A specific example of the improved high volume bypass filter is shown in FIGS. 2-6. In FIGS. 2-6, the same numerals refer to the same parts of the illustrated bypass filter.

The bypass filter illustrated in FIGS. 2-6 comprises a bottom member 100, a top member 102, an ultrafiltration packet 104, two mesh spacers 106, and a sealing means 107. Bolt openings 108 are provided in the top and bottom members. Bolts 109 can be threaded within those bolt openings to clamp the ultrafiltration packet 104, the two mesh spacers 106, and the sealing means 107 between bottom member 100 and top member 102.

In order to understand how the ultrafiltration device functions, it will be necessary to have some understanding of the construction of the mesh spacers 106 and the ultrafiltration packet 104 in the Pellicon Cassette System. The ultrafiltration packet comprises a planar generally rectangular highly porous support having its upper and lower surfaces covered with ultrafiltration membranes. The ultrafiltration membrane is usually made of a material such as polysulfone, polyethylene, or an ether or ester cellulosic derivative such as cellulose acetate, cellulose propionate, cellulose butyrate, methyl cellulose or ethyl cellulose, among others. Generally, modified cellulose acetate is a preferred membrane and can be cast from a solution comprising cellulose acetate, acetone and formide. The membrane may also contain varying amounts of filler particles. Reference can be made to U.S. Pat. Nos. 3,170,867; 3,310,488; 3,344,214; 3,446,359,; and 3,593,855 and *Chemical Engineering*, Sept. 4, 1972, pp. 56–73, for detailed information concerning such membranes and their preparation. Generally, the ultrafiltration membranes will have an average pore size diameter in the range of about 10 to about 15 Angstrom Units.

The highly porous support for the ultrafiltration membranes is constructed of such material that permits filtrate flow throughout. The support is further constructed of such material as to reinforce the ultrafiltration membranes against rupture when those membranes are forced against the support by fluid pressure.

Figure 3:
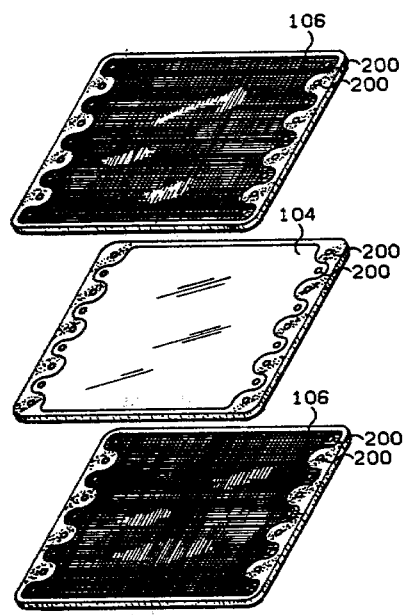
FIG. 3 is a diagrammatic perspective view illustrating the mesh supports and ultrafiltration packet that are employed in a bypass filter as illustrated in FIG. 2.
Figure 4:
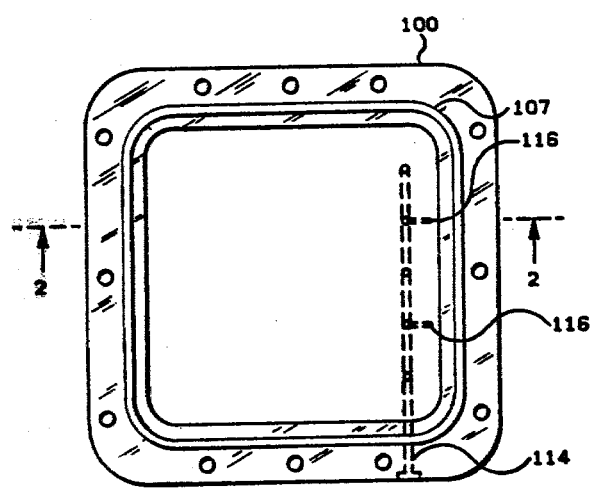
FIG. 4 is a top plan view of the bottom member of the bypass filter illustrated in FIG. 2.
Figure 5:
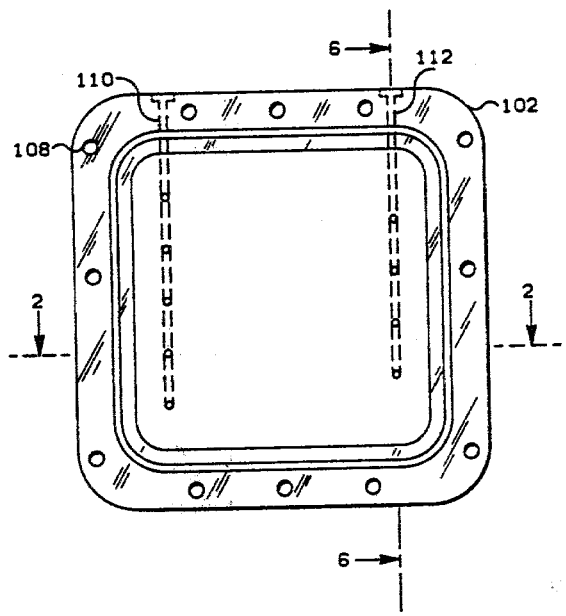
FIG. 5 is a bottom plan view of the top member of the bypass filter illustrated in FIG. 2.
Figure 6:
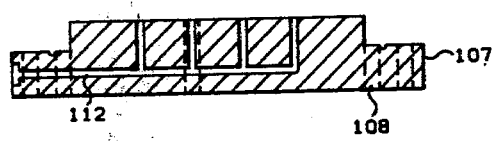
FIG. 6 is a cross-section view taken along line 6—6 of FIG. 5.

Referring now to FIG. 3, it will be noted that in each of two opposite ends of the ultrafiltration packet there are a plurality of holes 200 which extend through the packet. The edges of the packet 104 are sealed by gluing. Further alternate holes 200 of the packet 104 are sealed off from communication with the membrane or the support by areas of gluing. The areas of gluing around the edges and the holes are illustrated by shading in FIG. 3.

The mesh spacers 106 also have holes 200 extending therethrough in such a fashion that when the spacers 106 and the packet 104 are properly stacked the holes of both match to provide passageways. The mesh spacers 106 also have their edges sealed by gluing. In addition, the holes of the spacers 106, corresponding to the unsealed holes of the packet 104, are sealed off from communication with the mesh area of the spacer by areas of gluing. Here again, the areas of gluing are illustrated in FIG. 3 by areas of shading.

When the packet and spacers are clamped in the bypass filter, the alternate gluing patterns around the holes of each define at each of the two opposite ends two series of separate passageways. One series of passageways at each end are filtrate passageways which are in fluid communication with the porous support of the packet 104 and which are not in fluid communication with the mesh spacers 106. The other series of passageways are fluid sample passageways which are sealed from fluid communication with the porous support of the packet.

The top member 102 has a sample inlet manifold 110 which provides fluid communication between a source of sample liquid and the fluid sample passageways of one end of the packet-spacer assembly. The top member 102 also has an outlet manifold 112 in fluid communication with the filtrate passageways of the opposite end of the packet-spacer assembly.

Also the bottom member 100 has an outlet manifold 114 connected to the fluid sample passageways of the same end of the packet-spacer assembly that is connected to the outlet manifold 112 of top member 102. Also, the bottom member 100 includes passageways 116 which provide for fluid communication between the outlet manifold 114 and the space between the packet-spacer assembly and the sealing ring 107.

When the bypass valve illustrated by FIGS. 2-6 is assembled and connected to a source of sample fluid, the sample fluid flows from inlet manifold 110 into the sample passageways beneath. The sample liquid from the sample passageways thus flows across both spacers 106 and into the sample passageways at the opposite end of the packerspacer assembly and then out of the bypass valve via outlet manifold 114. By connecting outlet manifold to a valve, sufficient backpressure can be built up in the bypass valve to force liquid in the spacers which is in contact with the packet 104, to flow through ultrafiltration membranes to produce a filtrate which flows through the porous support of packet 104 into the filtrate passageways of the packet-spacer assembly. The filtrate in the filtrate passageway then flows out of the bypass valve via outlet manifold 112.

Any liquid which leaks out of the packet-spacer assembly will be trapped in the surrounding space that is sealed by sealing ring 107. Liquid flowing into that space then is combined via passageways 116 with the retentate in outlet manifold 114 which then passes out of the bypass filter.

It is to be understood that the specific filter illustrated in FIGS. 2-6 is just one example of such a bypass filter of the present invention. Various modifications and alterations of the illustrated device will be within the scope of the instant invention. For example, the inlet and outlet manifolds do not necessarily have to be in the top and bottom members as specified. Instead, those manifolds can be in any arrangement consistent with the proper functioning of the device. Also, if desired, one can include a second filtrate outlet manifold connected to the filtrate passageways at the end of the packet-spacer assembly that is connected to the sample inlet manifold. Other such variations will be readily conceived by those skilled in the art having the benefit of this disclosure. It is further to be noted that while this inventive bypass filter has been described as especially suitable for the aforedescribed system of analyzing beer, it has application for any of those situations in which such ultrafilters are generally employed.

Another type of bypass filter that can be employed in the inventive system illustrated in FIG. 1 is that of the type disclosed in U.S. Pat. No. 3,459,307, the disclosure of which is hereby incorporated by reference. That type of bypass filter comprises a filter body, an inlet in the filter body to allow the fluid to be filtered to enter the filter body, a first outlet in the filter body to allow filtrate to exit the filter body, a filter means separating the inlet and the first outlet, and a second outlet in open communication with the inlet to allow material too large to flow through the filter to exit the filter body as retentate. For use in the system illustrated in FIG. 1, the filter means used in such a bypass valve comprises a suitable ultrafiltration membrane.

A further embodiment of the present invention includes a self-cleaning filtering apparatus having improved resistance to blockage of the filter means by an undesirable buildup of high molecular weight material on the surface of that filter means. This apparatus includes a bypass filter having features specified above for the bypass filter of U.S. Pat. No. 3,459,307. The system further comprises an inlet line connected to the inlet of the bypass filter. The inlet line contains a fluid eductor. An outlet line in fluid communication with the eductor is connected to the retentate outlet of the bypass filter. The eductor is positioned such that when sample fluid is flowed through the eductor, that flow will draw fluid from the retentate outlet line into the inlet line. A valve is included in the outlet line for maintaining backpressure in the bypass filter. Between the valve and the eductor is included an outlet from the outlet line. Within the flow path defined by the outlet line, eductor inlet line, and bypass filter there is contained a plurality of solid clearing particles that are too large to pass through the filter means of the bypass filter. A filter means is included in the outlet of the outlet line which prohibits the solid cleaned particles from passing out of that outlet while allowing materials of smaller particle size to pass through that outlet.

The solid cleaning particles can include any solid particles which are of a size which is readily circulated through the system and which assist in the cleaning of the filter means of the bypass filter. Of course, preferably cleaning particles are selected that do not tend to dissolve or disintegrate in use. Generally, particles of about 5 to about 100 microns particle size are suitable. The presently preferred particles have a particle size in the range of about 10 to about 30 microns. Examples of suitable cleaning particles include, for example, metal powders, such as zinc or zinc oxide, or ferric oxide; fly ash, cement, and carbon black particles.

Figure 7:
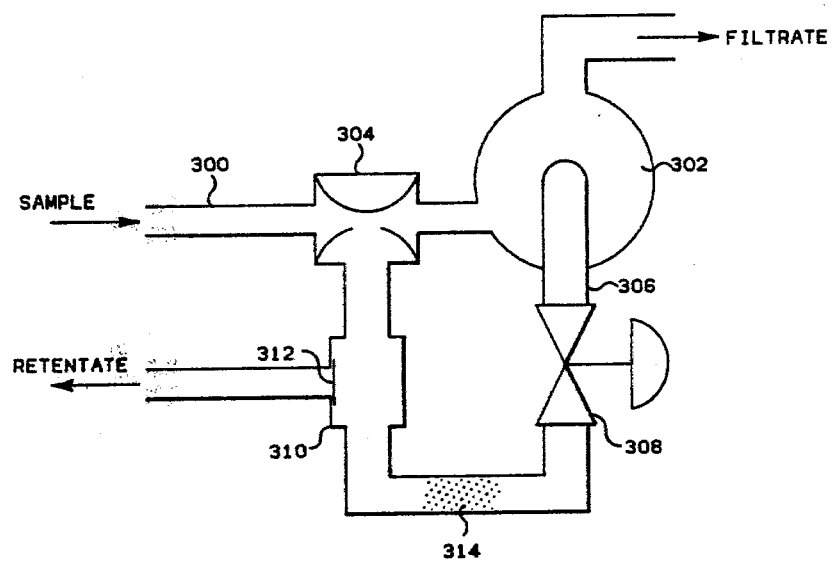
FIG. 7 is a schematic representation of an inventive self-cleaning filtering apparatus having improved resistance to blockage of the filter by high molecular weight materials in the sample stream.

A schematic illustration of such an inventive apparatus is provided in FIG. 7. In that drawing, an inlet line 300 is connected to the inlet of bypass filter 302. An eductor 304 is located in the inlet line 300. An outlet line 306 is connected to the retentate outlet of bypass filter 302 and to the eductor 304. A backpressure valve 308 is contained in line 306. A second bypass filter 310, with its associated filter means 312, is located in outlet line 306 in such a manner as to provide the outlet line 306 with a filtered outlet. Finally, solid clearing particles 314 are included within the outlet line 306.

In operation, as sample flows through inlet line 300 and into bypass filter 302, filtrate and retentate will exit from bypass filter 302. Also, the solid cleaning particles along with some retentate will be drawn from outlet line 306 into inlet line 300 by the sample flowing through eductor 304. The continuous recirculation of the cleaning particles effects a scouring of the surface of the filter means in bypass filter 302 which assists in prohibiting undesirable buildups of high molecular weight materials on the filter means of bypass filter 302.

While the invention illustrated in FIG. 7 is particularly suitable for use in the beer analysis system illustrated in FIG. 1, it is to be understood that the invention also finds application for any uses in which it is desired to reduce buildup of high molecular weight material or large particle size materials on the filter means of such bypass filters.

Still another bypass filter that can be employed in the inventive system illustrated in FIG. 1 is an inventive bypass filter similar in some respects to the bypass filters of the type disclosed in above mentioned U.S. Pat. No. 3,459.307, This new and improved type of bypass filter comprises a pair of filter means separated by a filter spacer. The filter means are secured between first and second filter body halves in a filtrate receiving cavity defined by adjoining portions of the filter body halves. Each filter half also contains a cavity therein which is open to a substantial amount of the adjoining surface of the adjoining filter means. Each filter body half further includes an inlet port communicating with the filter body half cavity in such a manner that when liquid is passed in that part it will flow around the periphery of the cavity in a swirling motion. Also, each filter body half includes a retentate outlet port allowing liquid to flow out of the cavity without passing through the adjoining filter means. The above mentioned filter spacer also contains a cavity providing communication between the first and second filter means. An outlet is provided in the filter spacer which provides fluid communication between the filter spacer cavity and the filtrate receiving cavity. Also a filtrate outlet port is included in the bypass filter in communication with the filtrate receiving cavity.

An illustration of one such bypass filter is provided by FIGS. 8-11. In FIGS. 8-11, identical numerals refer to identical features.

Figure 8:
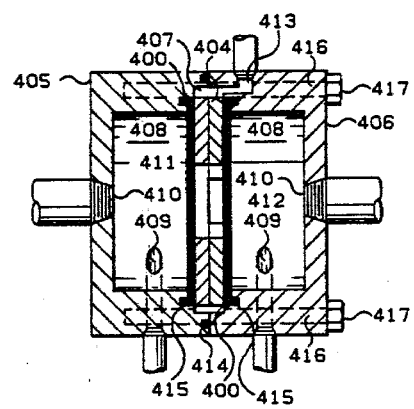
FIG. 8 is a cross-sectional view of another new improved bypass filter which is included as an embodiment of the present invention.
Figure 9:
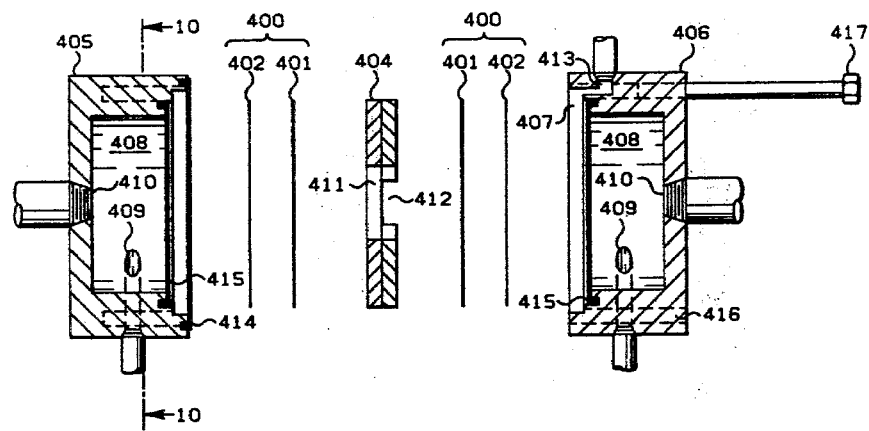
FIG. 9 is a cross-sectional exploded view of the bypass filter illustrated in FIG. 8.
Figure 10:
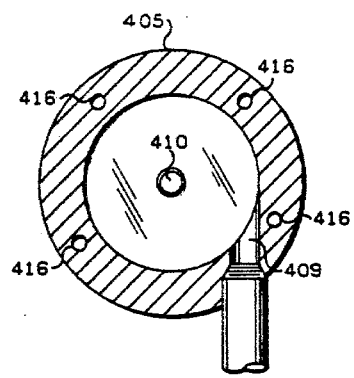
FIG. 10 is a cross-sectional view taken along line 10—10 of FIG. 9.
Figure 11:
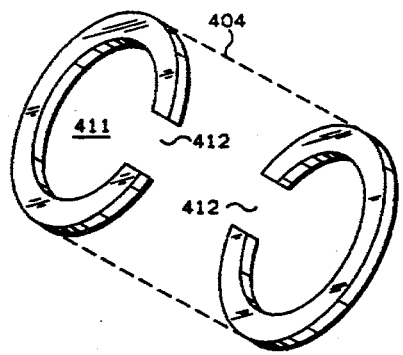
FIG. 11 is a perspective view illustrating the construction of the filter spacer means of the bypass filter illustrated in FIG. 8.

The bypass filter of FIG. 8 includes two filter means 400 each comprising an ultrafiltration filter 401 and a fine mesh gauze 402. The filter means 400 are each separated by a filter spacer means 404 which, as illustrated in FIG. 11, comprises two reversely disposed adjoining C-rings. Preferably, the C-rings would be firmly secured to each other by welding, gluing, or some other suitable technique. The two filter means 400 and the filter spacer 404 are secured between filter body halves 405 and 406. The filter body halves 405 and 406 when joined define a filtrate receiving cavity 407 in which the two filter means 400 and the filter spacer means 404 are secured. Each filter body half 405 and 406 includes another cavity 408 therein which is open to a substantial amount of the adjoining surface of the adjoining filter means. Each filter body half also has an inlet port 409 communicating with the cavity 408 such that it enables incoming liquids to enter tangentially with respect to cavity 408 to set up a circular, swirling, washing action in cavity 408. Each filter body half also has outlet port 410 opposite filter means 400 through which retentate may exit cavity 408.

The filter spacer 404 contains a cavity 411 providing for open communication between the two filter means 400. Further, the filter spacer includes two openings 412 which provide for communication between cavity 411 and filtrate receiving cavity 407. And body half 406 includes an outlet port 413 which will allow filtrate to flow from the filtrate receiving cavity 407 out of the bypass filter.

An O-ring seal 414 or other suitable sealing means is mounted on body half 405 in such a fashion as to provide a seal around the filtrate receiving cavity 407 when body halves 405 and 406 are assembled. Further, body halves 405 and 406 each have attached O-rings 415 or other suitable sealing means to seal the adjoining filter means 400 around the adjoining perimeter of the respective cavity 408.

The filter body halves 405 and 408 are also provided with bolt holes 416 into which bolts 417 can be threaded to secure the filter body halves in their assembled position.

In operation of this inventive bypass valve, liquid from a process stream is flowed into the cavities 408 of filter body halves 405 and 406 so that the liquid swirls in a circular fashion in each cavity. With the retentate outlets 410 connected to valved conduits which maintain necessary backpressure within cavities 408, liquid and materials not blocked by the filter means 400 will flow into cavity 411 and out openings 412 into the filtrate receiving cavity 407. From the filtrate receiving cavity, the thus obtained filtrate exits the bypass valve via outlet 413.

The swirling motion of the liquid within the cavities 410 assists in preventing large particles from accumulating on the adjoining side of the filter means 400 in such amounts as would seriously inhibit the production of filtrate. Since the two filter means 400 are in fluid communication with each other, the flow of liquid from the spacer cavity 411 to the filtrate receiving cavity 407 also assists in preventing the large particle materials in the liquid sample from blocking the filter means 400.

Generally the ultrafiltration filter will comprise an ultrafiltration membrane and a porous support which abuts the filter spacer means 404. While an ultrafiltration filter means is required in the bypass valve of FIG. 8 when it is to be employed in the system of FIG. 1, it is to be noted that bypass filters of the type illustrated in FIG. 8 can also be employed in systems in which one is not interested in obtaining filtrates of the type obtained with ultrafilters. Therefore it follows that filter means 400 can be any suitable filter, including commercially available microporous membranes. Also while for a system such as that illustrated in FIG. 1. it is desirable for the filter means to include the fine mesh gauze 402, the gauze is not absolutely essential for even that system.

In a preferred embodiment of this invention the fine mesh gauze 402 is designed to filter out material greater than 100 microns in size and the ultrafiltration filter 401 is designed to filter out material greater than 10 microns in size.

In another especially preferred embodiment, the fine mesh gauze 402 of filter means 400 of this filter is the polyethylene gauze sold by Kimre, Inc. of Perrine, Fla. as Mist Eliminator, Style 4196 under the trademark B-Gon. This polymeric fiber mesh is constructed so that each surface has parallel runs of square raised portions having therebetween inverted pyramidal portions. This particular structural pattern assists in imparting additional mixing of the liquid in cavities 408 and thus contributes in preventing undesirable blockages of filter means 400.

Clearly, bypass filters of the type illustrated by FIG. 8 can, if desired, have included in association with each filter body half cleaning particle recycling means such as described in connection with FIG. 7. Such a modification will provide additional assurance against undesirable filter blockage.

Although in the preceding discussion several specific embodiments of the present invention have been disclosed herein for the purposes of illustration, it should be understood that further variations and modifications of the structure, materials and uses disclosed and discussed herein may be made without departing from the spirit of the invention the scope of which is defined by the following claims.

What is claimed is:

1. A method for continuously analyzing individual streams of a plurality of streams of beverage containing carbon dioxide comprising passing each stream individually, at a pressure sufficient to prevent significant degassing of the beverage, through a filter means which separates said beverage into retentate containing materials of greater than a preselected molecular weight and a filtrate comprising substantially materials of less than said preselected molecular weight, passing said filtrate also under pressure sufficient to prevent significant degassing to a liquid column chromatographic analysis system wherein a sample of said filtrate is subjected to chromatographic analysis under pressure sufficient to prevent significant degassing of the filtrate sample.

2. An analytical system for the continuous analysis of beverages which comprises:
   (1) at least one sample stream line each said line adapted to be connected to a separate process line containing the beverage to be analyzed,
   (2) a bypass filter means capable of separating a stream of beverage into a retentate and a filtrate containing no significant amounts of material having more than a predetermined molecular weight,
   (3) a manifold means in fluid communication with each sample stream line,
   (4) an outlet line providing fluid communication between said manifold means and said bypass filter means,
   (5) first pumping means in each sample stream line at a point sufficiently below the juncture of the process line and the sample stream line to assure that when said first pumping means is operated there will not be any significant degassing of the beverage,
   (6) a second pumping means in said outlet line for pumping beverage to said bypass valve,
   (7) a recycle line providing fluid communication between each sample stream line at a point between said manifold and said first pumping means in said sample stream line back to the respective process line,
   (8) recycle valve means associated with each sample stream line for controlling whether the sample stream will flow to the manifold or to the process line,
   (9) a retentate line providing for flow of retentate from said bypass filter means,
   (10) an analyzer means capable of measuring the amount of at least one chosen low molecular weight material in the beverage filtrate,
   (11) a filtrate line providing for flow of filtrate from the bypass filter to said analyzer means,
   (12) a filtrate disposal line providing for flow of unanalyzed filtrate from said analyzer, and
   (13) back pressure regulator means connected to said filtrate disposal line and said retentate line so as to assure that the beverage in said system is maintained under sufficient pressure to prevent significant degassing of the beverage.

3. A system according to claim 2 including a valve control means for controlling the recycle valves.

4. A system according to claim 3 wherein said filtrate disposal line and said retentate line are joined at a point between the bypass filter and the back pressure regulator.

5. A system according to claim 2 wherein said bypass filter comprises a top member, a bottom member, a sample inlet means, a retentate outlet means, a filtrate outlet means, at least one ultrafiltration packet positioned between said top member and said bottom member, a mesh spacer above and below each said packet, means for clamping said at least one packet and the corresponding mesh spacers between said top and bottom members, means to flow liquid sample through each mesh spacer along the adjoining surface of the adjoining packet and then out of said bypass filter and means to allow filtrate from within each said packet to flow out said retentate outlet means, and means to allow filtrate from within each said packet to flow out said filtrate outlet means; means for sealing an area surrounding the said at least one ultrafiltration packet and the corresponding mesh spacers against leakage of liquid outside said bypass filter and means for removing from the bypass filter liquid which accumulates in that area.

6. A system according to claim 2 wherein said bypass filter comprises a top member, a bottom member, a sample inlet means, a retentate outlet means, a filtrate outlet means, at least one ultrafiltration packet positioned between said top member and said bottom member, a mesh spacer above and below each said packet, means for clamping said at least one packet and the corresponding mesh spacers between said top and bottom members, means to flow liquid sample through each mesh spacer along the adjoining surface of the adjoining packet and then out of said bypass filter and means to allow filtrate from within each said packet to flow out said retentate outlet means, and means to allow filtrate from within each said packet to flow out said filtrate outlet means.

7. A system according to claim 2 wherein said bypass filter comprises
   a bypass filter comprising a filter body, an inlet in said filter body to allow the fluid to be filtered to enter said filter body, a first outlet in said filter body to allow filtrate to exit the filter body, a filter means separating said inlet and said first outlet, and a second outlet in open communication with said inlet such as to allow material too large to flow through the filter means to exit the filter body,
   an inlet line connected to the inlet of said bypass filter,
   a fluid eductor in said inlet line,
   a retentate outlet line connected to the second outlet of said bypass filter so as to provide communication between said second outlet of said bypass filter and said fluid eductor, said eductor being positioned such that liquid flowing through said inlet line will draw liquid from the retentate outlet line into said inlet line,
   a valve in said retentate outlet line for maintaining backpressure in said bypass filter,
   an outlet in said retentate outlet line at some point between said valve and said eductor,
   a plurality of solid cleaning particles in the flow loop defined by the retentate outlet line, the eductor, the inlet line and the bypass filter,
   and a filter means in the outlet of said retentate outlet line, said filter means being such that it prohibits the solid cleaning particles from passing out the outlet of said retentate outlet line which allowing materials of samller particle size to pass out of said outlet.

8. A system according to claim 2 wherein said bypass filter comprises first and second filter means separated by a filter spacer and secured between first and second filter body halves in a filtrate receiving cavity defined by adjoining portions of said first and second filter body halves; wherein said first and second filter body halves each contain a cavity therein open to a substantial amount of the adjoining surface of the adjoining filter means, an inlet port communicating with said filter body half cavity in such a manner that when liquid is passed into said port it will flow around the periphery of said cavity in swirling motion, and a retentate outlet port allowing liquid to flow out of said cavity without flowing through the adjoining filter means; wherein said filter spacer further contains an outlet providing for communication between said filter spacer cavity and said filtrate receiving cavity; and wherein there is a filtrate outlet port in communication with said filtrate receiving cavity to allow filtrate to flow out of said bypass filter.

9. A system according to claim 8 wherein said bypass filter further comprises sealing means between the two filter body halves and between each filter body half and the adjoining perimeter of each filter means.

* * * * *